July 14, 1953 H. M. TIRET Plant Pat. 1,202
FUCHSIA PLANT
Filed Feb. 27, 1952
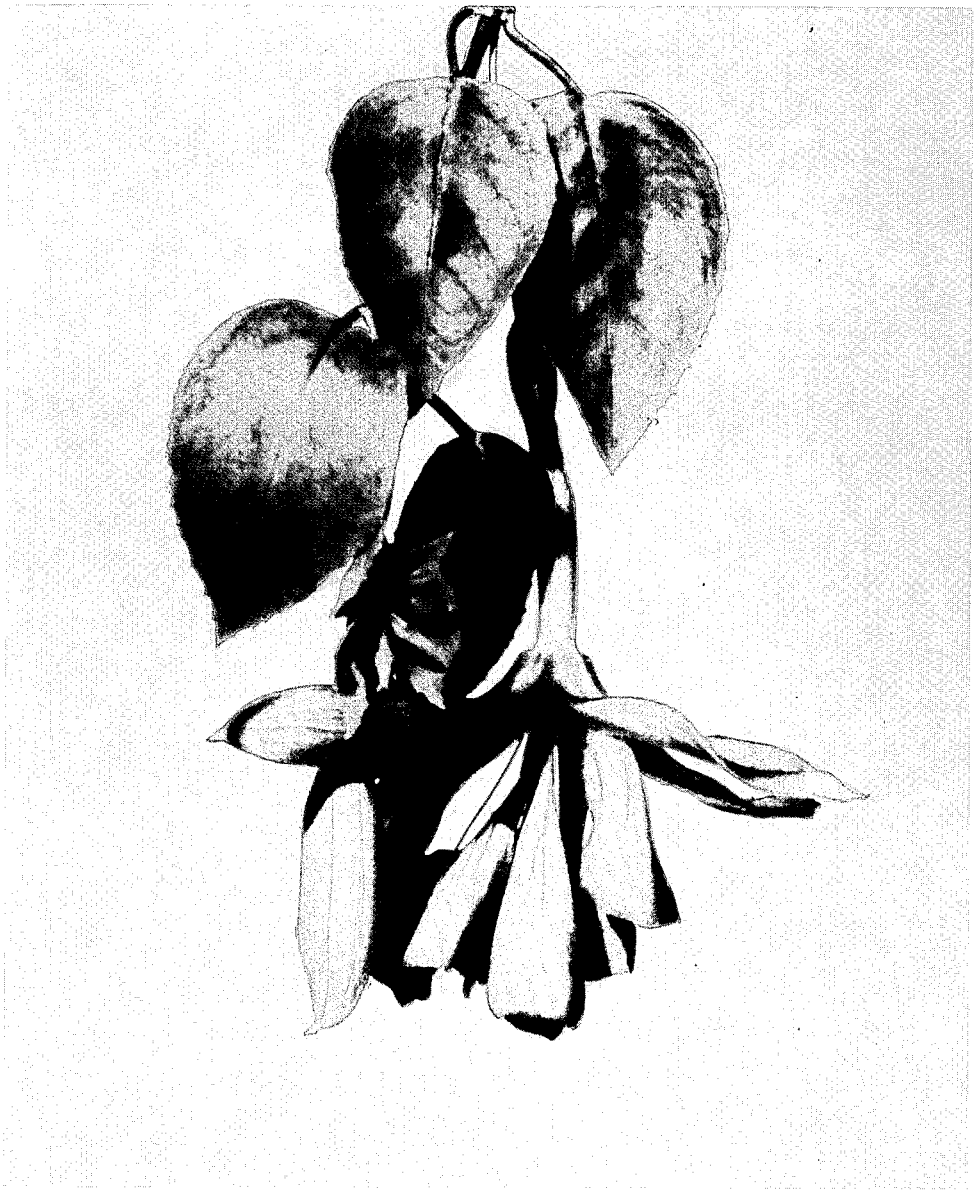
Inventor
Horace M. Tiret Patented July 14, 1953

Plant Pat. 1,202

UNITED STATES PATENT OFFICE 1,202

FUCHSIA PLANT

Horace M. Tiret, San Francisco, Calif.

Application February 27, 1952, Serial No. 273,705

1 Claim. (Cl. 47—60)

This invention relates to a new and improved fuchsia plant, the principal new and different characteristic of which is the distinctive form, resembling that of an orchid, and the exceptionally large size.

The plant was derived as a hybrid from Titanic (unpatented) of Victor Reiter, Jr., and Yuletide (unpatented) of applicant. The fuchsia plant is distinguished principally by its smooth, medium dark green and medium sized foliage, vigorous habit of growth, distinctive deep petunia purple coloring of the petals, all combined to accentuate its orchid like form, which has not previously been found in this combination and size in any fuchsia plant. The plant has been asexually reproduced at Palo Alto, California, by cuttings which retained the characteristics of the parent fuchsia.

The plant is a trailing variety, but may also be trained as an upright, and grows vigorously, throwing numerous branches during the process of growth. When the plant blooms, the extra large, crimson buds open into exceptionally large orchid-like flowers. The bud is medium crimson (Horticultural Color Chart 22/1). The outer area is deep petunia purple (Horticultural Color Chart 32). The flower has no fragrance.

In the accompanying drawing, the figure shows a typical branch tip and fully opened blossom, the drawing representing approximately actual size.

A detailed description of this new variety of fuchsia plant follows:

*Habit of growth.*—Strong trailing variety which throws out branches from the roots and whose branches in turn are self-branching to form a full basket. Flowers occur both along the stem and at the tips of the branches.

*Foliage.*—Medium dark green and medium sized leaves evenly spaced along the branch. The leaves are of a general, slender heart shape, having serrated edges, and tapering to pointed tips. The buds are short and broad, ovoid in shape, and colored a medium crimson.

*Flower.*—The flower is very double, of exceptionally large size for the genus. The corolla is open, with the outer petals flaring to horizontal. The flower is strongly resistant to wilting at high atmospheric temperature, but grows equally well in the cooler coastal climate of the west. The color of the outer petals is medium crimson (Horticultural Color Chart 22/1) at the base and down the center. The outer area of the center petals is deep petunia purple (Horticultural Color Chart 32). The inner petals are veined with crimson (Horticultural Color Chart 22/1) from the base to the center, with the outer area deep petunia purple (Horticulural Color Chart 32).

*Ovary.*—Small and slender, green in color.

*Tube.*—Thick and short, deep crimson in color.

*Petals.*—From fifteen to twenty-five petals occur to each flower, and the outer petals are exceptionally flaring, creating an open arrangement. As the flower matures, the petals retain their open, flaring form, resulting in the orchid-like form described. The petals are petunia purple accented by medium crimson, all as above described.

*Stamens.*—The stamens are long, approximately 2⅛ inches in length, measured from the seed pods, and of a dark maroon color, and terminate short of the long pistil, approximately 3¾ inches in length, measured from the seed pod, having a maroon tip which hangs below the cluster of stamens.

*Sepals.*—The sepals are long, broad, colored pale crimson on the underside and dark crimson on the outer surface. The texture is crepe like on the underside and smooth on the outer surface.

*Parentage.*—Titanic (unpatented) by Victor Reiter, Jr., and Yuletide (unpatented) by applicant.

It is noted that the foliage and flowers will vary somewhat with the season and growing condition; however, the fuchsia plant is clearly differentiated from others by the orchid-like form and exceptionally large size.

Having thus disclosed my discovery I claim:

The new and distinct variety of fuchsia plant herein described and illustrated, characterized by the exceptionally large size of the flower and the deep petunia purple coloring, combined with the orchid-like form.

HORACE M. TIRET.

References Cited in the file of this patent

UNITED STATES PATENTS

| Number | Name | Date |
|---|---|---|
| Pl. Pt. 1,100 | Waltz | July 1, 1952 |